United States Patent
Tsoukalis

[19]

[11] Patent Number: 5,980,490
[45] Date of Patent: Nov. 9, 1999

[54] LINEAR PERISTALTIC PUMP

[75] Inventor: Alexandre Tsoukalis, Athens, Greece

[73] Assignee: Micrel, Microelectronic Applications Center Ltd., Greece

[21] Appl. No.: 09/023,355

[22] Filed: Feb. 13, 1998

[30] Foreign Application Priority Data

Feb. 17, 1997 [GR] Greece ................................ 970100064

[51] Int. Cl.[6] .................................................. A61M 1/00
[52] U.S. Cl. ........................................... 604/151; 417/474
[58] Field of Search ............................. 604/151; 417/474

[56] References Cited

U.S. PATENT DOCUMENTS

| | | |
|---|---|---|
| 2,412,397 | 12/1946 | Harper ..................................... 417/474 |
| 5,078,683 | 1/1992 | Sancoff et al. . |
| 5,165,873 | 11/1992 | Meijer ..................................... 417/474 |

FOREIGN PATENT DOCUMENTS

| | | |
|---|---|---|
| 0 069 350 A1 | 1/1983 | European Pat. Off. . |
| 0 225 158 A2 | 6/1987 | European Pat. Off. . |
| 0 431 726 | 6/1991 | European Pat. Off. . |
| 0 560 270 | 9/1993 | European Pat. Off. . |
| 0941672 | 7/1982 | U.S.S.R. ................................ 417/474 |
| 20 20 735 | 11/1979 | United Kingdom . |
| WO 84/00690 | 3/1984 | WIPO . |

*Primary Examiner*—Jeffrey A. Smith
*Attorney, Agent, or Firm*—Ware, Fressola, Van der Sluys & Adolphson LLp

[57] ABSTRACT

The invention relates to linear peristaltic pump of known contruction, in which a first cam (30*a*) and a first cam follower (11*a*) in the form of an input valve, at least three intermediate cams (30*b*–30*e*) and cam followers (11*b*–11*e*) for pumping operation and a last cam (30*f*) and a last cam follower (11*f*) in the form of an output valve are used.

16 Claims, 6 Drawing Sheets

LINEAR PERISTALTIC PUMP

DESCRIPTION

The invention relates to a linear peristaltic pump comprising linear peristaltic pump comprising a resilient tube supported on a support plate and having an input end connected to a fluid reservoir as well as an output end; a motor-driven cam shaft rotatably supported in parallel to the flexible tube and having at least three cams which are displaced angularly to each other; a cam follower for each cam for reciprocating movement in a direction normal to the axis of the cam shaft and having end faces for squeezing the flexible tube in an operation sequence travelling along the tube from the input end to the output end. Such a linear peristaltic pump is known from EP-B1-0 560 270.

Whereas syringe pumps have the disadvantage of low capacity of the fluid reservoir containing the fluid to be infused, so that the reservoir would have to be changed quite often, particularly for long time infusions, peristaltic pumps are also not without disadvantages or problems. One problem is that of back flow meaning that a portion of the infused liquid mixed with blood of the patient is returned back into the needle if the blood pressure is higher than the internal pressure of the peristaltic pump. This is particularly a problem at low infusion rates, because blood remaining in the canula needs special treatment by trained persons, so that homecare treatment would not be possible. Moreover, there is the danger of thrombosis. The volume of infused fluid might also vary in dependence on the pressure difference between the blood pressure and the internal pressure in the peristaltic pump.

It is an object of the present invention to avoid these disadvantages of the prior art peristaltic pumps, and to provide a linear peristaltic pump which avoids back flow, and in which the volume of infusion can be accurately metered without dependence on the blood pressure etc. of the patient.

In accordance with the invention, a linear peristaltic pump, is characterized by a first cam and a first cam follower in the form of an input valve for opening and closing the flexible tube at the input end, at least one intermediate cam and cam follower for pumping operation, and a last cam and a last cam follower in the form of an output valve for opening and closing the flexible tube at the output end.

A preferred embodiment is characterized in that each of the intermediate cams has three curve portions, namely a first portion with a continuously increasing radius for the pressing phase, a second, circumferential portion with a constant radius equal to the radius at the end of the first portion for maintaining the flexible tube closed, and a third portion with a sharp decrease of the radius for quick release of the tube. Preferably, the last cam driving the last cam follower, has an extended circumference portion with a large radius, for closing the tube while pressure is built up by the intermediate cam followers inflating the tube, and further has a smaller radius at the end of a transition portion large enough to keep the tube at least at a level where passing of liquid is just possible.

In order to arrive at a continoues, constant flow of infusion fluid into the patient line, an additional flow linearizing cam at the end of the infusion mechanism is provided, having an increasing radius portion with a maximum radius while the last cam is having its larger radius, and a decreasing radius portion for the rest of the rotation, the smallest radius being that is needed to its cam follower just touch the tube. In order to extend the linearizing range, preferably the end face or finger of the cam follower of the flow linearizing cam has a larger length, preferably twice the length, in the longitudinal direction of the flexible tube than the other cam followers.

A preferable means of measuring the internal pressure of the peristaltic pump as well as the pressure in the output line to the patient, i. e. under normal circumstances the blood pressure of the patient, without the need of two pressure transducers is characterized by providing an ultra-low displacement pressure transducer placed on the support plate under the resilient tube at a longitudinal position of the flexible tube between the first cam follower and the last cam follower, the upper surface of the pressure transducer being flush with the upper surface of the support plate; position sensor means for sensing a first position of the cam shaft, at which the first cam follower has its closed position, and a second position at which the last cam follower has its closed position, thereby allowing to determine the downstream pressure in the patient line when the first position is detected, and the upstream pressure within the enclosed pressurized liquid inside the peristaltic pump when the second position is detected, from the output signal of the pressure transducer. Since the pressure transducer is placed beneath the resilient tube on the opposite side of the cam followers, it is not necessary to provide additional space between the cam followers for pressure transducers as is the case in prior art peristaltic pumps. The same pressure transducer can therefore be used to measure the upstream pressure present within the enclosed pressurized liquid inside the peristaltic pump, or the downstream pressure present in the patient line.

The output signal of the pressure transducer either represents the downstream pressure of the upstream pressure, depending on the angular position of the cam shaft when the pressure signal is measured. These two angular positions of the cam shaft can either be measured by sensor means consisting of two separate position or angle sensors, each detecting one of the first and second positions, or by electronic position sensor means having a saw-tooth generator generating a saw-tooth signal in synchronism with the rotation of the cam shaft, from which the first and second positions are detected by discriminators from different signal levels of the saw-tooth signal.

Since the pressure measuring means as defined above provide precise pressure measurements on the upstream side (internal pressure of the peristaltic pump) and the downstream side (patient line), the pressure measurements of the pressure transducer can be used for obtaining status information about reservoir empty, leaks in the system, occlusion pressure, canula out of vein and/or air in patient line.

A problem in infusion pumps is the presence of air in the system and the syphoning of fluid into the patient line when the peristaltic pump is in a position where the fluid flow is not stopped. In accordance with a preferred embodiment, an air eliminating filter and an anti-syphon valve are permanently connected in series with the patient line.

Further preferred embodiments are defined in the dependent claims.

The invention is now described in connection with preferable embodiments of the invention in connection with the accompanying drawings.

Figure 1:
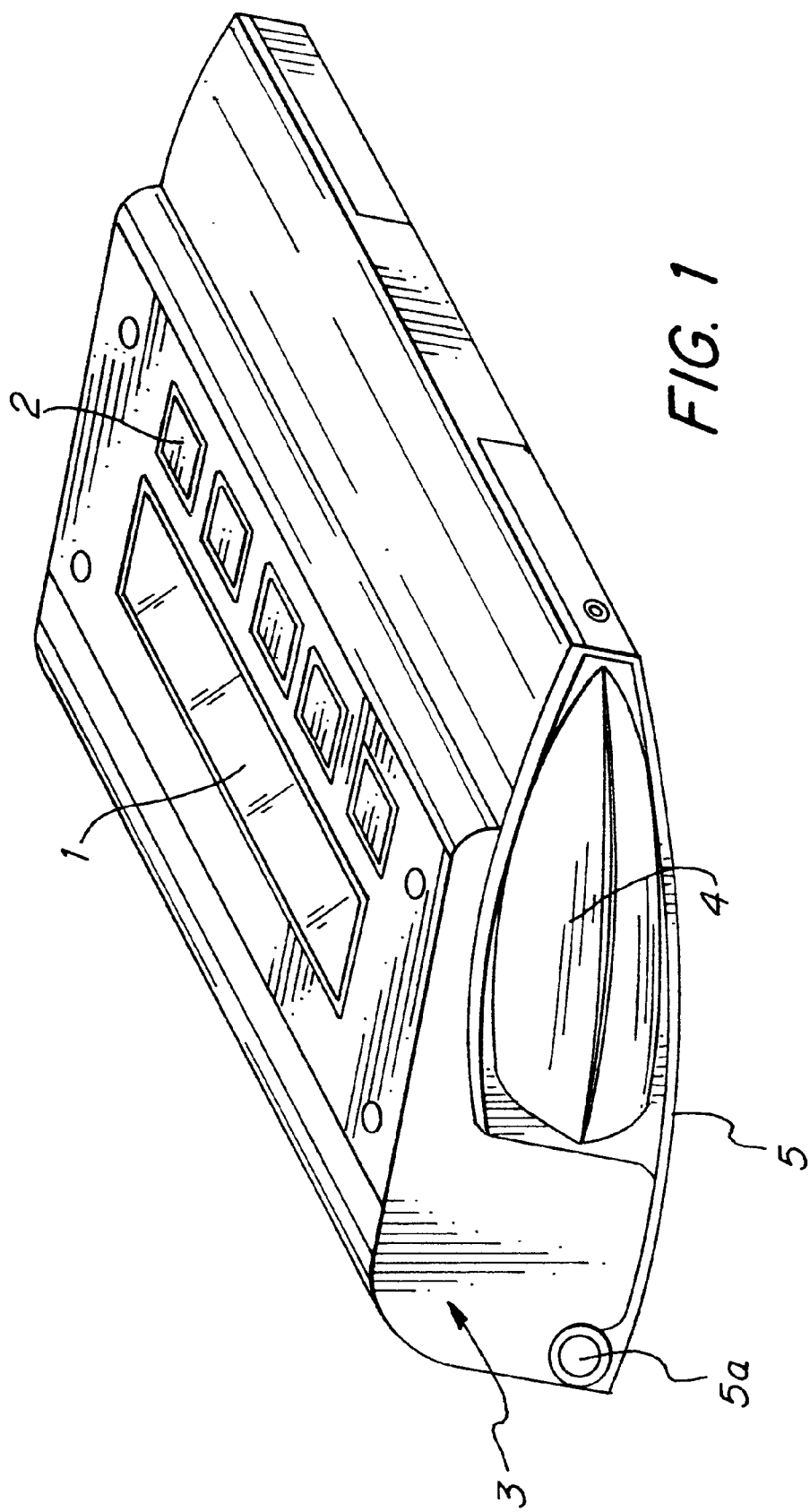
FIG. 1 shows a perspective general view of the linear peristaltic pump according to the invention.

The general view of the linear peristaltic pump, FIG. 1, shows a housing 3 containing the mechanical parts of the pump including a motor, a reduction gear, an electric battery and the movement mechanism in the area of the rear part, whereas in a lower front part of the housing 3 the electronics are installed. The housing 3 is provided with a lid 5 at the bottom hinged at 5a for access to a compartment into which an exchangeable unit comprising a fluid reservoir 4 can be inserted. At the top of the housing, a display 1 and operation keys 2 are provided.

Now, the pumping mechanism shall be described in connection with FIGS. 2 and 3 of the drawings. A cam shaft 9 having a plurality of cams 30, namely cams 30a–30g, is rotatably supported by journals 8 within a stationary frame 26. The cam shaft 9 is driven by a low inertia motor 6 having a reduction gear 6a. A rotational position encoder 7 including a sensor 17 is provided in order to detect the speed of rotation and angular position of the cam shaft 9. The signals of the sensor 17 are used by the electronics for controlling the operation of the peristaltic pump, as will be later explained in detail.

Corresponding to each of the cams 30a–30g, there is provided a plurality of cam followers 11, namely cam followers 11a–11g, each cam follower 11 having a small ball bearing 10 supported with is inner part 10a on a projection 38 formed at the cam followers 11. The outer circumference 10b of each ball bearing 10 touches the cam surface of each cam 30a–30g, so that only small friction is present between the cam followers 11 and the cams 30a–30g.

End faces 37 or fingers of the cam followers 11 operate on a flexible tube 16 supported on a support plate 5, being the lid for the housing 3 as already mentioned. The cam followers 11 are guided for movement in a straight line in vertical direction (as seen in the drawings) by side faces 36 moving in guide faces 26a in the form of grooves present in side walls of the stationary frame 26.

Figure 2:
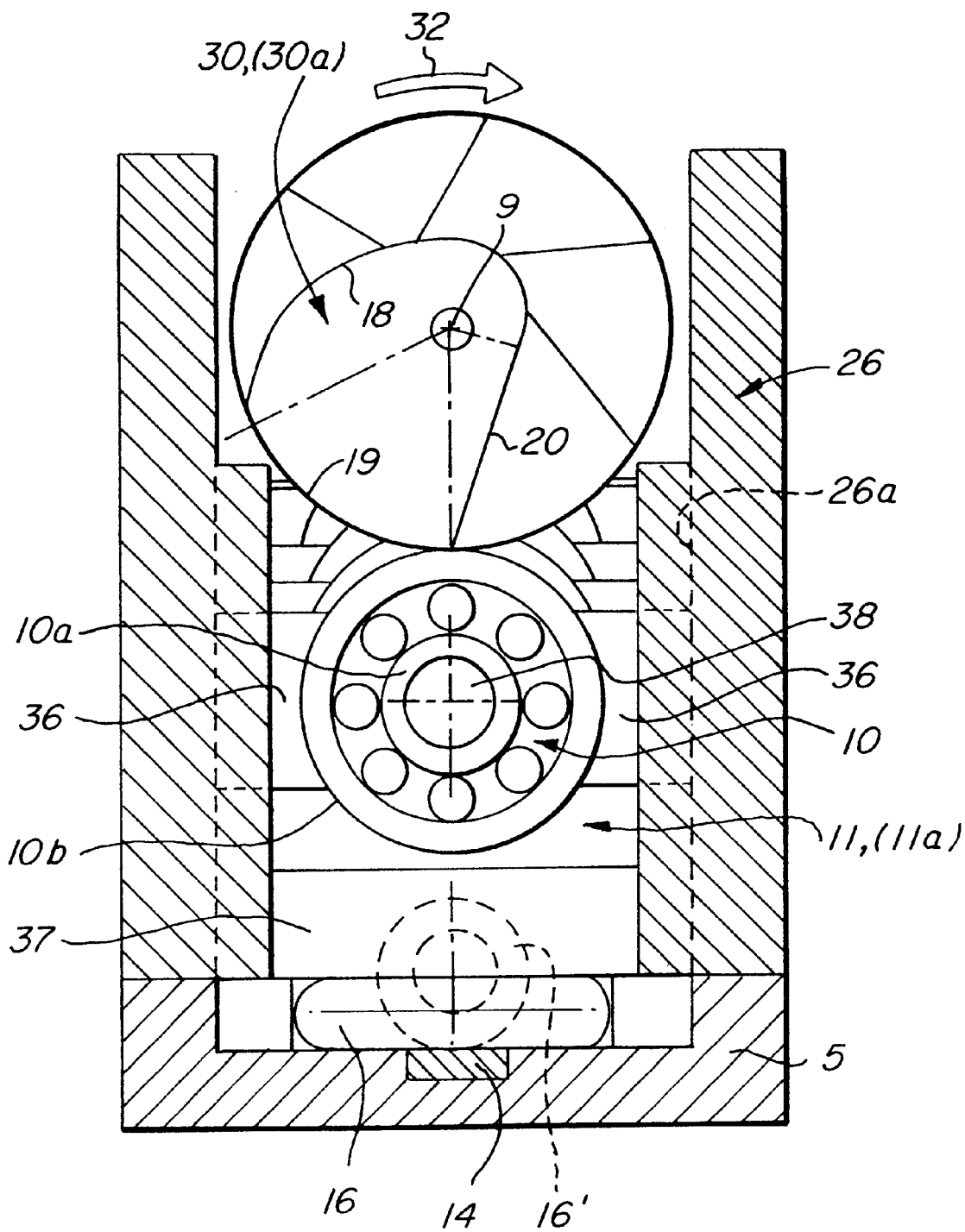
FIG. 2 shows a cross section through the pumping mechanism, showing the cam shaft, cam followers with ball bearings and the flexible tube.
Figure 3:
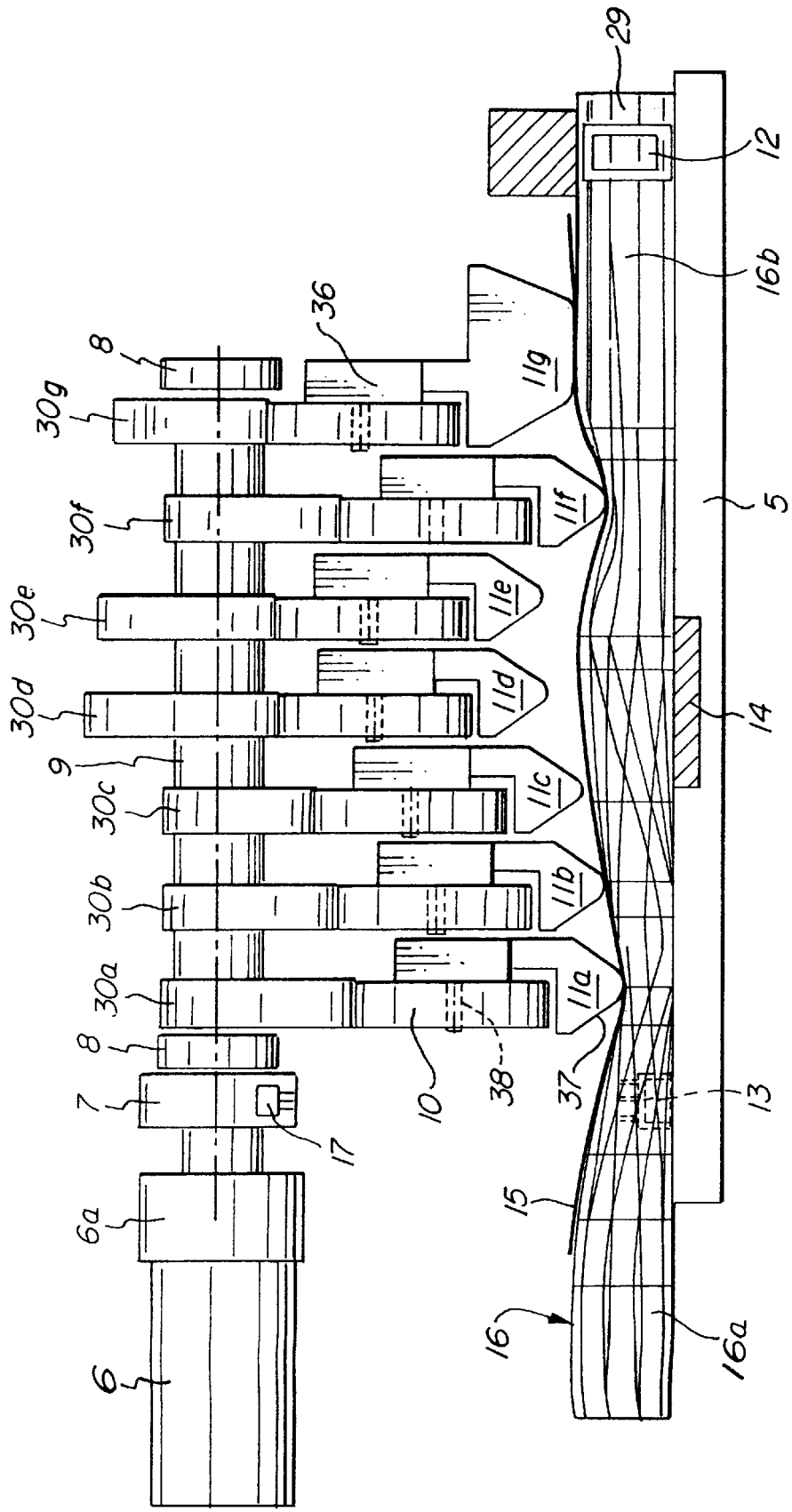
FIG. 3 shows a side view of the pumping mechanism of the peristaltic pump.

From FIGS. 2 and 3 it can be seen that the end face 37 or finger of the cam follower 11a of the first cam 30a has fully squeezed the flexible tube 16 to its closed position (the dotted lines showing the flexible tube 16' in its fully open position). The individual cams 30, namely cams 30b–30e, have all substantially the same shape but are displaced angularly to each other by 60°. This displacement provides for a substantially even torque load to the motor 6. In FIG. 3, the input end 16a of the flexible tube 16 is seen on the left side of the drawing, whereas the output end 16b is shown on the right side.

The flexible tube 16 is made of elastic material, preferably of silicone material. To seal the flexible tube 16 against the drive mechanism, a protective sheet 16 of plastic material is placed between the tube 16 and the end faces 37 of the cam followers 11a–11g (only shown in FIG. 3 but not in FIG. 2 for the sake of clarity).

Figure 6:
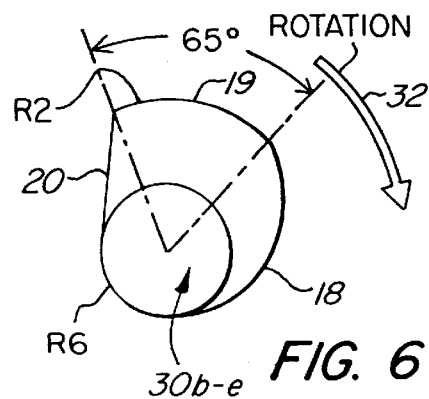
FIG. 6 shows a side view of one of the regular cams.

The intermediate cams 30b–30e see FIGS. 2, 3 and 6 have three portions of curvature, i.e.

a first portion 18 having a continuously increasing radius of calculated curvature for the pressure phase, a second portion 19 having a constant radius R2 equal to the radius at the end of the first portion 18 for maintaining the flexible tube 16 fully closed, and a third portion 20 having a sharp decrease of the radius to a small radius R6 for quick release of the tube 16.

From FIG. 2 it can be seen that, although the stroke of the cams 30 can be rather large, the width of the mechanism (seen in horizontal direction of FIG. 2) does not need to be much larger than the maximum outer diameter of the cams 30. The bearings 10 which can be small, only take space in the squeezing direction, and the sliding support of the cam followers 11 within the stationary support 26 safeguards a linear guidance in the squeezing direction.

The cam followers 11 are pushed upwards by the elasticity of the tube 16 upon release by the cam followers 11. It is, however, also possible to assist the upward movement by return springs.

Figure 4A:
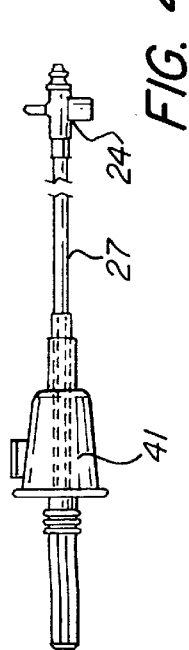
FIG. 4a shows an alternative solution.
Figure 4:
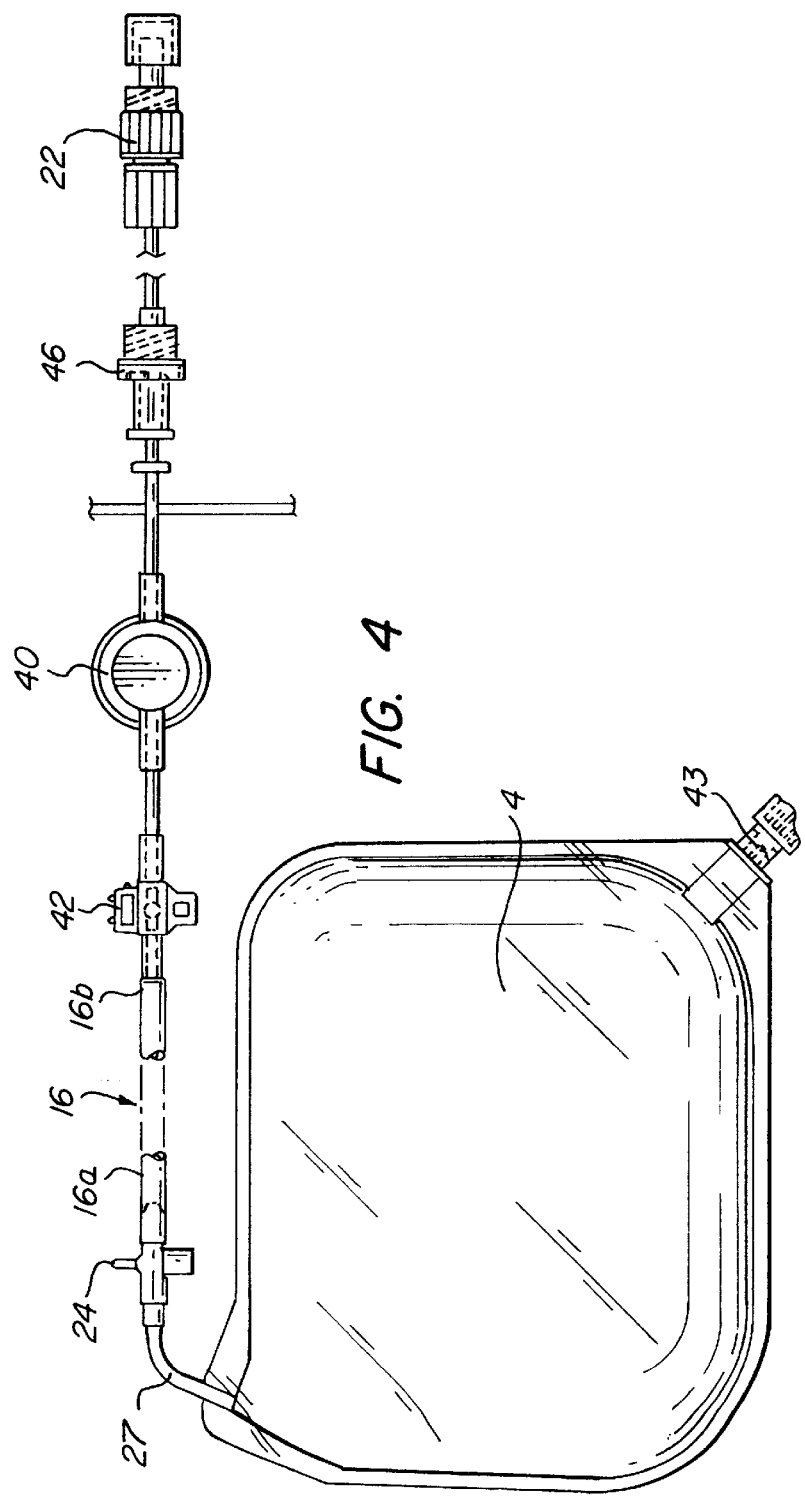
FIG. 4 shows a schematic view of a fluid reservoir, the flexible tube and the fluid line system.

FIG. 4 now shows a fluid system comprising a fluid reservoir 4 in the form of a small bag preferably made from soft elastomer material, and the flexible tube 16 being connected through a pump connector 24 and an input tube 27 to the fluid reservoir 4. The output end 16b of the flexible tube 18 is connected through a second connector 42, an air bubble eliminating filter 40, and an anti-syphon valve 46 to an output connector 22 in the form of a Luer Lock connector 22, to the patient line.

FIG. 4a is a modification of the fluid system in that the flexible tube 16 is connected trough a pump connector 24 and an input tube 27 with a syringe or needle device 41 to be inserted into a standard collapsible supply bottle or reservoir for supply instead of an integrated reservoir 4 as shown in FIG. 4.

As already described in connection with FIG. 1, the exchangeable unit comprising the fluid reservoir 4 and the flexible tube 16, can be inserted into a compartment of the housing 3 by opening the hinged lid 5 at the bottom of the housing 1. Moreover, as can be seen in FIG. 3, a switch 13 is provided which is operated by the lid 5 in such a way that operation of the peristaltic pump is only permitted when the lid 5 is properly closed.

Now, more details of the shape of the intermediate cams 30b–30e shall be described in connection with FIG. 6. As already mentioned in connection with FIGS. 2 and 3, each of the cams 30b–30e has a first portion 18 having a continuously increasing radius of calculated curvature, and in the present embodiment, this portion extends over an angle of 200°. The radius of the cam surface preferably increases linearly with the rotation angle in the direction of an arrow 32. The subsequent second portion 19 has a constant radius, i.e. the maximum radius R2. In the present embodiment, the portion 19 lasts for 65°. In the third portion 20 a sharp decrease from the maximum radius R2 to a minimum radius R6 takes place, in the present embodiment during a rotation angle of about 95°. The maximum radius R2 and the length of the cam followers 11 are such that the flexible tube 16 is completely closed. Although in FIG. 3, the end faces 37 of some of the cam followers 11 are shown at a distance from the flexible tube 16, this distance or gap is smaller or zero in practice.

In the preferred embodiment, four intermediate cams 30b–30e and corresponding cam followers 11b–11e are shown. This leads to a smooth pumping action. It is possible to have even more intermediate cams and cam followers, there must be at least one, in addition to the input cam 30a and the output cam 30f. In such cases the durations of the cam phases must be adapted.

Figure 5:
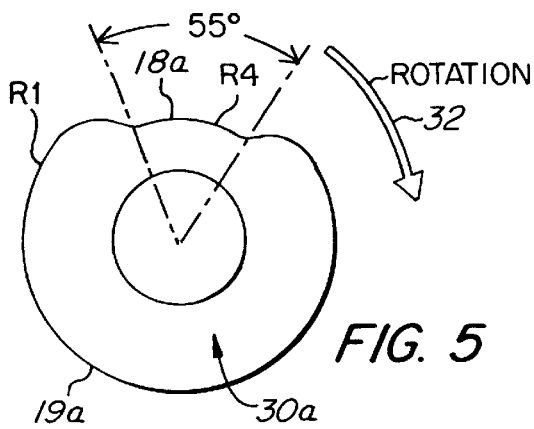
FIG. 5 shows a side view of the first cam.

Referring now to FIG. 5, the shape of the first cam 30a controlling the first cam follower 11a is described. In contrast to the intermediate cams 30b, 30c, 30d and 30e, the first cam 30a has two parts, namely a first part 19a with a large radius R1, and a second part 18a having a smaller radius R4. The part 18a having the smaller radius R4 extends over a range of approximately 55°, during which the tube 16 is only opened so much as needed for the filling process, whereas during the other part 19a the tube 16 is completely closed.

Figure 7:
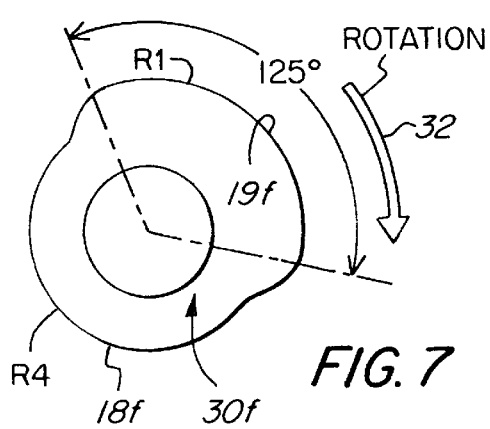
FIG. 7 shows a side view of the last cam.

The last cam 30f as shown in FIG. 7, also differs from the intermediate cams 30b, 30c, 30d and 30e. In fact, a second, circumferential portion 19f, having a large radius R1, is extended by a certain range, preferably by 60°, as compared with the circumferential part 19 of the cams 30b–30e, i.e. the circumferential part 19f extends over a range of 65°+60°= 125°, during which flexible the tube 16 is fully closed. In the remaining portion 18f of the last cam 30f, the radius R4 of the cam is such that the tube 16 is slightly compressed to such a value that the flow of fluid is permitted.

Figure 8:
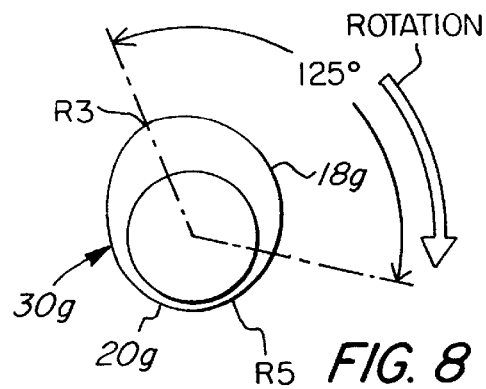
FIG. 8 shows a side view of an additional cam for equalizing the output fluid volume.

FIG. 8 now shows an additional, linearizing cam 30g which is placed behind the sixth other cams 30a–30f (FIG. 3) for the purpose of smoothing variations of the flow of fluid at the output during the pumping action. As FIG. 8 shows, the additional cam 30g has a first portion 18g during which the radius increases from a minimum radius R5 to a maximum radius R3. From this maximum value R3 the radius decreases during a second portion 20g to the minimum radius R5 again. The maximum radius R3 is smaller than the maximum radii R1, R2 of the other cams 30a–30f because the volume of the flexible tube 16 shall only be decreased but not closed. The angular duration of the first portion 18g is about 125°, whereas the remaining portion 20g is about 235°. While the output valve 11f is closed, liquid is expulsed by the flow linearizing cam follower 11g so that the output flow is not stopped, thus linearizing the flow.

Now, the function of the flow linearizing cam 30g shall described in connection with FIGS. 7 and 8 of the drawings. When the last cam 30f closes the flexible tube 16 as an output valve during the portion 19f, cam 30g proceeds through its phase 18g increasing its radius from the minimum radius R5 to the maximum radius R3, so that fluid already at the end of the flexible tube 16 is pumped into the patient line. During the open phase 18f of the last cam 30f, when fluid passes the output valve, the flow rate to the patient line is slightly decreased by the flow linearizing cam 30g when proceeding through part 20g where the cam 30g reduces its radius from the maximum radius R3 to the minimum radius R5. In fact, the flow rate is equal to the higher positive flow of the intermediate cam followers 11b–11f plus the reduction by the linearizing cam follower 11g, leading to a substantially constant flow rate. The reservoir 4 is provided with a filling valve 43 which is activated by a syringe (not shown) for refilling the reservoir 4.

Figure 9:
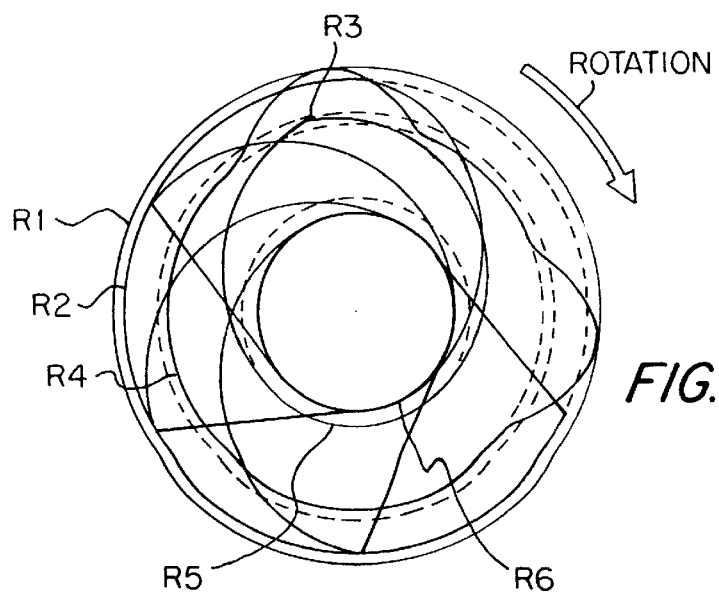
FIG. 9 shows a superposition view of all cams.

FIG. 9 shows a superposition of all cams 30a–30g showing the various curve shapes as well as the various radii R1–R6. The largest maximum radius R1 which is present at the first and the last cams 30a and 30f fully compresses the flexible tube 16 to a pressure of 3 bar. A slightly reduced radius R2 which is present at the intermediate cams 30b–30e only leads to a pressure of 1 bar. Radius R3 is the maximum radius of cam 30g and just closes the flexible tube 16. Radius R4 is the smallest radius for the first and last cams 30a and 30f and keeps the flexible tube just open. Radius R6 of the linearizing cam 30g is the minimum radius which keeps the flexible tube 16 fully open. Finally, radius R6 is used in the intermediate cams 30b–30e and holds the flexible tube 16 away, not even touching it, for accuracy independent from manufacturing tolerances.

While normally the lengths of the end faces 37 of the cam followers 11a–11g are the same in the longitudinal directions of the cam shaft 9 and the flexible tube 16, FIG. 3 shows that the length of cam follower 11g is longer than those of the other cam followers 11a–11f. The length of the linearizing cam follower 11g is shown about twice the length of the others in order to increase the linearizing function in view of the long close time of 125° of the last cam follower 11f. The length of the linearizing cam follower 11g can even be larger than twice the length of the others.

Figure 10:
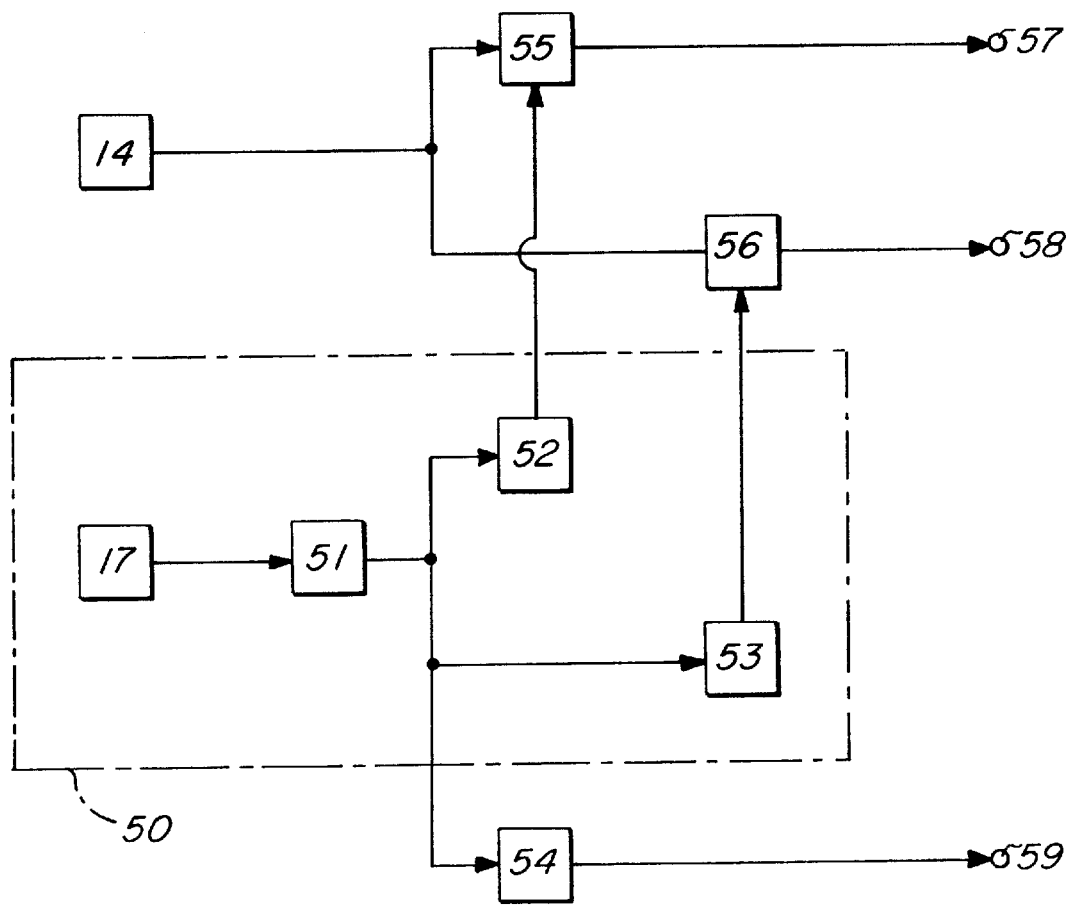
FIG. 10 shows a block diagram of position sensor and pressure measuring means.

With reference to the block diagram of FIG. 10, the position sensor and pressure measuring means shall be described. The encircled block 50 represents an electronic positions sensor means for generating two position signals of the cam shaft 9, namely a first position at which the first cam follower 11a has its closed position, and a second position at which the last cam follower 11f has its closed position. A position sensor 17 detects a certain position of a drum 7 rotating with the cam shaft 9 (see FIG. 3), and a saw-tooth generator 51 generates a saw-tooth signal from the output signal of the position sensor 17. Each revolution of the cam shaft 9 generates one period of the saw-tooth signal. Two discriminators 52 and 53 are provided for outputting output signals as selected signal levels of the saw-tooth signal, these levels corresponding to the angular position of the cam shaft 9. The output signals of the discriminators 52 and 53 are shown to control gates 65, 56, so that an output signal of the pressure sensor 14 is either sent to an output 57 as an output pressure signal of the downstream pressure, or to an output 58 for outputting the pressure signal as an upstream pressure signal. Furthermore, the crests of the saw-tooth signal of saw-tooth generator 51 are converted by a digitizer 54 into a speed output signal at an output 59. This speed output signal is not only used for control of the motor speed, but this signal is also used to meter the volume of the peristaltic pump by counting the revolutions of the cam shaft 9.

While the processing of the pressure signals by gates 55, 56 is shown as a hardware solution for explanation purposes, it is clear that this task is normally performed in a microprocessor by an interupt function.

Instead of providing an electronic position sensor means 50, it is also possible to control the gate inputs of gates 55 and 56, or a microprocessor, by the output signals of two different position sensors each detecting one of the two positions of the cam shaft 9.

By measuring two pressure values under certain conditions within the flexible tube 16 by the pressure transducer 14, it is possible to detect 5 possible situations:

1. Reservoir empty: low pressure upstream before the opening of the output valve (cam 30f, cam follower 11f).
2. Leaks in the system: this is indicated by medium to low upstream pressure before opening of the output valve 30f, 11f.
3. Occlusion pressure: this is indicated by high downstream pressure after opening the output valve 30f, 11f.
4. Canula out of vein: this is indicated by low downstream pressure after opening of the output valve 30f, 11f.
5. Air in patient line: this is indicated by medium tb low upstream pressure before opening of the output valve. Since liquids are non-compressible, pressure is built-up by a limited number of other cam followers while the input and output valves are closed, which induces a relatively higher pressure in the absence of air when the elastic tube 16 inflates to increase its volume capacity depending on the tube expansion and elasticity. If compressible air exists in the tube 16, the tube expansion is less, so that the measured pressure value is also lower.

I claim:

1. Linear peristaltic pump comprising:
   (a) a support plate:
   (b) a flexible tube supported on the support plate and having an input end connected to a fluid reservoir as well as an output end; and
   (c) Pumping operation device for squeezing the flexible tube in an operation sequence traveling along the flexible tube from the input end to the output end, the pumping operation device comprising:
      (i) a motor-driven cam shaft having an axis and being rotatable supported in parallel to the flexible tube,
      (ii) an input valve for opening and closing the flexible tube at the input end, the input valve having a first cam on the cam shaft and a first cam follower mounted for reciprocating movement in a direction normal to the axis of the cam shaft and provided with an end face for squeezing the flexible tube,
      (iii) at least one intermediate cam angularly displaced on the cam shaft relative to the first cam and an intermediate cam follower for each intermediate cam, each intermediate cam follower being mounted for reciprocating movement in a direction normal to the axis of the cam shaft and having an end face for squeezing the flexible tube, the at least one intermediate cam and each cam follower mounted to perform a pumping operation, wherein each of the at least one intermediate cam has three curve portions, namely a first portion with a continuously increasing radius for a pressing phase, a second, circumferential portion with a constant radius equal to the radius at the end of the first portion for maintaining the flexible tube closed, and a third portion with a sharp decrease of the radius for quick release of the flexible tube, and
      (iv) an output valve for opening and closing the flexible tube at the output end, the output valve having a last cam angularly displaced on the cam shaft relative to the first cam and the at least one intermediate cam, the output valve also having a last cam follower mounted for reciprocating movement in a direction normal to the axis of the cam shaft and provided with an end face for squeezing the flexible tube.

2. Linear peristaltic pump according to claim 1, wherein the last cam driving the last cam follower has an extended circumference portion with a large radius for closing the tube while pressure is built up by each intermediate cam follower thereby inflating the flexible tube, and the last cam further has a smaller radius at the end of a transition portion large enough to keep the flexible tube at least at a level where passing of liquid is just possible.

3. Linear peristaltic pump according to claim 2, wherein the at least one intermediate cam is four intermediate cams arranged with angular displacements between the four intermediate cams of 60°, the second, circumferential portion of the four intermediate cams is about 65°, and the extended circumferential portion of the last cam is extended by 60° to 125°.

4. Linear peristaltic pump according to claim 3, wherein the first cam and the first cam follower open the flexible tube only as much as needed for a filling process, the first cam follower travelling from an open position to a closed position, the first cam follower being in the closed position except during the filling process during which the last cam follower is in a closed position.

5. Linear peristaltic pump according to claim 1, wherein each of the at least one intermediate cam between the first and the last cams compresses the flexible tube through its intermediate cam follower at a smaller pressure than the input valve and the output valve, each of the at least one intermediate cam having a large radius at its second circumferential portion which is smaller than a large radius of the first and last cams.

6. Linear peristaltic pump comprising:
   (a) a support plate;
   (b) a flexible tube supported on the support plate and having an input end connected to a fluid reservoir as well as an output end; and
   (c) pumping operation device for squeezing the flexible tube in an operation sequence traveling along the flexible tube from the input end to the output end, the pumping operation device comprising:
      (i) a motor-driven cam shaft having an axis and being rotatable supported in parallel to the flexible tube,
      (ii) an input valve for opening and closing the flexible tube at the input end, the input valve having a first cam on the cam shaft and a first cam follower mounted for reciprocating movement in a direction normal to the axis of the cam shaft and provided with an end face for squeezing the flexible tube,
      (iii) at least one intermediate cam angularly displaced on the cam shaft relative to the first cam and an intermediate cam follower for each intermediate cam, each intermediate cam follower being mounted for reciprocating movement in a direction normal to the axis of the cam shaft and having an end face for squeezing the flexible tube, the at least one intermediate cam and each cam follower mounted to perform a pumping operation,
      (iv) an output valve for opening and closing the flexible tube at the output end, the output valve having a last cam angularly displaced on the cam shaft relative to the first cam and the at least one intermediate cam, the output valve also having a last cam follower mounted for reciprocating movement in a direction normal to the axis of the cam shaft and provided with an end face for squeezing the flexible tube, and
      (v) an additional flow linearizing cam on the cam shaft after the last cam and having a linearizing cam follower mounted for reciprocating movement in a direction normal to the axis of the cam shaft, the linearizing cam having an increasing radius portion with a maximum radius corresponding to a largest radius on the last cam, the linearizing cam also having a decreasing radius portion for a remainder thereof, the linearizing cam having a smallest radius so that the linearizing cam follower just touches the flexible tube.

7. Linear peristaltic pump according to claim 6, wherein the linearizing cam follower has an end face with a larger length in a longitudinal direction of the flexible tube than the end faces of the first, intermediate and last cam followers.

8. Linear peristaltic pump comprising.
   (a) a support plate;
   (b) a flexible tube supported on the support plate and having an input end connected to a fluid reservoir as well as an output end;

(c) pumping operation device for squeezing the flexible tube in an operation sequence traveling along the flexible tube from the input end to the output end, the pumping operation device comprising:
  (i) a motor-driven cam shaft having an axis and being rotatable supported in parallel to the flexible tube,
  (ii) an input valve for opening and closing the flexible tube at the input end, the input valve having a first cam on the cam shaft and a first cam follower mounted for reciprocating movement in a direction normal to the axis of the cam shaft and provided with an end face for squeezing the flexible tube,
  (iii) at least one intermediate cam angularly displaced on the cam shaft relative to the first cam and an intermediate cam follower for each intermediate cam, each intermediate cam follower being mounted for reciprocating movement in a direction normal to the axis of the cam shaft and having an end face for squeezing the flexible tube, the at least one intermediate cam and each cam follower mounted to perform a pumping operation, and
  (iv) an output valve for opening and closing the flexible tube at the output end, the output valve having a last cam angularly displaced on the cam shaft relative to the first cam and the at least one intermediate cam, the output valve also having a last cam follower mounted for reciprocating movement in a direction normal to the axis of the cam shaft and provided with an end face for squeezing the flexible tube; and
(d) an ultra-low displacement pressure transducer placed on the support plate under the flexible tube at a longitudinal position of the flexible tube between the first cam follower and the last cam follower, the pressure transducer for producing an output signal, an upper surface of the pressure transducer being flush with an upper surface of the support plate.

9. Linear peristaltic pump as claimed in claim 8, further comprising position sensor means for sensing a first position of the cam shaft at which the first cam follower is in a closed position and a second position at which the last cam follower is in a closed position thereby allowing to determine downstream pressure when the first position is detected from the output signal of the pressure transducer and upstream pressure within enclosed pressurized liquid inside the peristaltic pump when the second position is detected from the output signal of the pressure transducer.

10. Linear peristaltic pump as claimed in claim 9, wherein the position sensor means comprise two separate position sensors, each detecting one of the first and second positions.

11. Linear peristaltic pump as claimed in claim 9, wherein the position sensor means include an electronic position sensor means having a saw-tooth generator generating a saw-tooth signal in synchronism as the cam shaft rotates, from which the first and second positions are detected by discriminators from different signal levels of the saw-tooth signal.

12. Linear peristaltic pump as claimed in claim 11, wherein crests of the saw-tooth signal are detected by a digitizer and used for speed control and counting of revolutions of a motor driving the cam shaft.

13. Linear peristaltic pump as claimed in claim 9, wherein the pressure transducer makes pressure measurements used for obtaining status information about:
  reservoir empty,
  leaks,
  occlusion pressure,
  canula out of vein, and
  air in patient line.

14. Linear peristaltic pump comprising:
(a) a support plate;
(b) a flexible tube supported on the support plate and having an input end connected to a fluid reservoir as well as an output end;
(c) pumping operation device for squeezing the flexible tube in an operation sequence traveling along the flexible tube from the input end to the output end, the pumping operation device comprising:
  (i) a motor-driven cam shaft having an axis and being rotatable supported in parallel to the flexible tube,
  (ii) an input valve for opening and closing the flexible tube at the input end, the input valve having a first cam on the cam shaft and a first cam follower mounted for reciprocating movement in a direction normal to the axis of the cam shaft and provided with an end face for squeezing the flexible tube,
  (iii) at least one intermediate cam angularly displaced on the cam shaft relative to the first cam and an intermediate cam follower for each intermediate cam. each intermediate cam follower being mounted for reciprocating movement in a direction normal to the axis of the cam shaft and having an end face for squeezing the flexible tube, the at least one intermediate cam and each cam follower mounted to perform a pumping operation, and
  (iv) an output valve for opening and closing the flexible tube at the output end, the output valve having a last cam angularly displaced on the cam shaft relative to the first cam and the at least one intermediate cam, the output valve also having a last cam follower mounted for reciprocating movement in a direction normal to the axis of the cam shaft and provided with an end face for squeezing the flexible tube; and
(d) an air eliminating filter and an anti-syphon valve permanently connected in series with a patient line.

15. Linear peristaltic pump as claimed in claim 14, further comprising a reservoir provided with a filling valve which is actuated by a syringe for refilling the reservoir.

16. Linear peristaltic pump comprising:
(a) a support plate;
(b) a flexible tube supported on the support plate and having an input end connected to a fluid reservoir as well as an output end;
(c) pumping operation device for squeezing the flexible tube in an operation sequence traveling along the flexible tube from the input end to the output end, the pumping operation device comprising:
  (i) a motor-driven cam shaft having an axis and being rotatable supported in parallel to the flexible tube,
  (ii) an input valve for opening and closing the flexible tube at the input end, the input valve having a first cam on the cam shaft and a first cam follower mounted for reciprocating movement in a direction normal to the axis of the cam shaft and provided with an end face for squeezing the flexible tube,
  (iii) at least one intermediate cam angularly displaced on the cam shaft relative to the first cam and an intermediate cam follower for each intermediate cam, each intermediate cam follower being mounted for reciprocating movement in a direction normal to the axis of the cam shaft and having an end face for squeezing the flexible tube, the at least one intermediate cam and each cam follower mounted to perform a pumping operation, and (iv) an output valve for opening and closing the flexible tube at the output end, the output valve having a last cam angularly displaced on the cam shaft relative to the first cam and the at least one intermediate cam, the output valve also having a last cam follower mounted for reciprocating movement in a direction normal to the axis of the cam shaft and provided with an end face for squeezing the flexible tube; and (d) a reservoir provided with a filling valve which is actuated by a syringe for refilling the reservoir.

* * * * *

UNITED STATES PATENT AND TRADEMARK OFFICE
CERTIFICATE OF CORRECTION

PATENT NO. : 5,980,490
DATED : November 9, 1999
INVENTOR(S) : Alexandre Tsoukalis It is certified that error appears in the above-identified patent and that said Letters Patent is hereby corrected as shown below:

In column 1, line 5, "linear peristaltic pump comprising" should be deleted.

In column 1, line 60, the spelling of "continuous" should be corrected.

In column 3, line 24, "Is" should be --is--.

In column 3, line 37, "is" should be --its--.

In column 3, line 62, "16" should be --15--.

In column 4, line 24, "18" should be --16--.

In column 4, line 29, "trough" should be --through--.

In column 5, line 38 after "shall", --be-- should be inserted.

In column 5, line 66, "R6" should be --R5--.

In column 6, line 31, "65" should be --55--.

In column 6, line 45, the spelling of "interrupt" should be corrected.

In column 6, line 65, "tb" should be --to--.

In column 7, line 66, "3" should be --2--.

In claim 1, line 11, claim 6, line 11, claim 8, line 11, claim 14, line 11 and claim 16, line 11, "rotatable" should be --rotatably--.

UNITED STATES PATENT AND TRADEMARK OFFICE
CERTIFICATE OF CORRECTION

PATENT NO. : 5,980,490
DATED : November 9, 1999
INVENTOR(S) : Alexandre Tsoukalis It is certified that error appears in the above-identified patent and that said Letters Patent is hereby corrected as shown below:

In the abstract, line 2, the spelling of "construction" should be corrected.

Signed and Sealed this

Eighth Day of August, 2000

Attest:

Q. TODD DICKINSON

*Attesting Officer*

*Director of Patents and Trademarks*